United States Patent
Banbury et al.

(10) Patent No.: US 9,717,681 B2
(45) Date of Patent: Aug. 1, 2017

(54) FORMULATIONS CONTAINING SUBSTITUTED IMIDAZOLE DERIVATIVES

(75) Inventors: Susan Banbury, Chettenham (GB); Päivi Juujärvi, Littoinen (FI); Leon Grother, Swindon (GB); Walter Lunsmann, Harvard, MA (US); Owen Murray, Green Brook, NJ (US); Juha-Matti Savola, Turku (FI)

(73) Assignee: R.P. Scherer Technologies, LLC, Las Vegas, NV (US)

( * ) Notice: Subject to any disclaimer, the term of this patent is extended or adjusted under 35 U.S.C. 154(b) by 1212 days.

(21) Appl. No.: 10/534,117

(22) PCT Filed: Nov. 3, 2003

(86) PCT No.: PCT/US03/34934
§ 371 (c)(1),
(2), (4) Date: Oct. 6, 2005

(87) PCT Pub. No.: WO2004/043439
PCT Pub. Date: May 27, 2004

(65) Prior Publication Data
US 2006/0134194 A1    Jun. 22, 2006

(30) Foreign Application Priority Data
Nov. 8, 2002 (GB) .................................. 02260768

(51) Int. Cl.
A61K 9/20 (2006.01)
A61K 31/4164 (2006.01)
A01N 43/50 (2006.01)
A61K 9/00 (2006.01)
A61K 47/26 (2006.01)
A61K 47/42 (2017.01)

(52) U.S. Cl.
CPC ............ A61K 9/0056 (2013.01); A61K 9/006 (2013.01); A61K 9/2095 (2013.01); A61K 31/4164 (2013.01); A61K 47/26 (2013.01); A61K 47/42 (2013.01)

(58) Field of Classification Search
USPC .......................................... 424/464; 514/396
See application file for complete search history.

(56) References Cited

U.S. PATENT DOCUMENTS

| | | | |
|---|---|---|---|
| 4,371,516 A | 2/1983 | Gregory et al. | |
| 4,855,326 A | 8/1989 | Fuisz | 514/777 |
| 4,946,684 A | 8/1990 | Blank et al. | |
| 4,968,692 A * | 11/1990 | Linnoila et al. | 514/396 |
| 5,079,018 A | 1/1992 | Ecanow | 426/385 |
| 5,292,887 A * | 3/1994 | Karjalainen et al. | 514/396 |
| 5,298,261 A | 3/1994 | Pebley et al. | 424/488 |
| 5,948,430 A | 9/1999 | Zerbe et al. | 424/435 |
| 5,976,577 A * | 11/1999 | Green et al. | 424/490 |
| 6,284,270 B1 | 9/2001 | Lagoviyer et al. | 424/464 |
| 6,316,026 B1 | 11/2001 | Tatara et al. | 424/464 |
| 6,316,027 B1 * | 11/2001 | Johnson et al. | 424/464 |
| 6,375,982 B1 | 4/2002 | Cherukuri | 424/484 |
| 6,552,024 B1 | 4/2003 | Chen et al. | 514/252.16 |
| 6,669,957 B1 | 12/2003 | Laruelle et al. | |
| 6,709,669 B1 * | 3/2004 | Murray et al. | 424/434 |
| 6,726,928 B2 * | 4/2004 | Yarwood et al. | 424/464 |

FOREIGN PATENT DOCUMENTS

| | | |
|---|---|---|
| EP | 0204045 | 12/1986 |
| EP | 0618906 | 4/1998 |
| EP | 0651997 B1 | 10/1998 |
| EP | 0974365 | 9/2004 |
| EP | 0914818 | 6/2005 |
| GB | 211423 | 2/1924 |
| GB | 1548022 | 7/1979 |
| JP | H07-506087 | 7/1995 |
| WO | WO 91/04757 | 4/1991 |
| WO | 93/13074 | 7/1993 |
| WO | WO 93/12769 | 7/1993 |
| WO | 95/00492 | 1/1995 |
| WO | WO 00/67694 | 11/2000 |
| WO | WO 01/19336 | 3/2001 |
| WO | WO 03/030881 | 4/2003 |

OTHER PUBLICATIONS

US 5,120,549, 06/1992, Gole et al. (withdrawn)
R. Huupponen, et. al., Clin. Pharmacol. Ther. 1995; 58:506-511.

* cited by examiner

*Primary Examiner* — Shirley V Gembeh
(74) *Attorney, Agent, or Firm* — Fitzpatrick, Cella, Harper & Scinto

(57) ABSTRACT

Improved formulations containing substituted imidazole derivatives of the general formula 1, formula (I) wherein Y is —$CH_2$— or —CO—, $R_1$ is H, halo or hydroxy, $R_2$ is H or halo, and $R_3$ is H or lower alkyl (e.g. $C_1$ to $C_4$ alkyl, preferably $C_1$ or $C_2$ alkyl), or a pharmaceutically acceptable salt, such as an acid addition salt, e.g. the hydrochloride, of a compound of the general formula (I), are in solid fast-dispersing dosage form suitable for pre-gastric absorption.

(I)

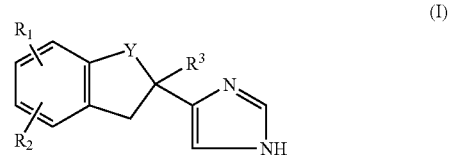

15 Claims, No Drawings

FORMULATIONS CONTAINING SUBSTITUTED IMIDAZOLE DERIVATIVES

RELATED APPLICATIONS

This application is based on International Application No. PCT/US2003/034934 filed 3 Nov. 2003 which claims priority to Application No. GB 0226076.8; filed 8 Nov. 2002.

This invention relates to improved formulations containing substituted imidazole derivatives and is more particularly concerned with such formulations where the substituted imidazole derivative is of the general formula (I)

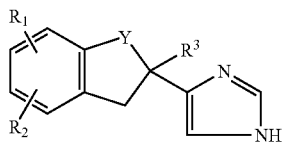

(I)

wherein Y is —$CH_2$— or —CO—, $R_1$ is H, halo or hydroxy, $R_2$ is H or halo, and $R_3$ is H or lower alkyl (e.g. $C_1$ to $C_4$ alkyl, preferably $C_1$ or $C_2$ alkyl), or a pharmaceutically acceptable salt, such as an acid addition salt, e.g. the hydrochloride, of a compound of the general formula (I).

The compounds of the above-mentioned formula (I) and their salts are highly selective and long-acting antagonists of $\alpha_2$-adrenoceptors and are especially valuable in the treatment of cognitive disorders. Compounds of formula (I) and their preparation have been described in EP-A-0 618 906. Specific examples of such compounds are 4-(2-ethyl-5-fluoro-2,3-dihydro-1H-inden-2-yl)-1H-imidazole and 4-(5-fluoro-2,3-dihydro-1-inden-2-yl)-1H-imidazole.

Although the compounds of formula (I) and their salts have good properties as such, they have disadvantages, when formulated for conventional oral administration, i.e. the normal route for administering said compounds into the stomach. It has been found that the compounds rather quickly decompose in the gastrointestinal area, which significantly lowers the effect of the compounds in question.

Atipamezole (4-[1-(2,3-dimethylphenyl)ethyl]-1H-imidazole mono-hydrochloride), an $\alpha_2$-adrenoceptor antagonist being one of the examples for the compounds of the present invention (I) has been shown to have increased bioavailability when administered as a buccal spray compared with per oral administration (R. Huupponen et. al. Clin. Pharmacol. Ther. 1995; 58:506-511). Absorption was found not to be proportional to dose (the relative amount absorbed decreased with increasing dose) and transient adverse reactions such as white spots and numbness were observed at the application site.

SUMMARY OF THE INVENTION

It has now been found that the above-mentioned problem can be avoided by formulating the compounds of formula (I) into fast-dispersing solid dosage forms so that they can be absorbed through the oral mucosal membrane or otherwise pre-gastrically.

According to the present invention, there is provided a fast-dispersing, solid dosage form containing, as an active ingredient, a substituted imidazole derivative of general formula (I):

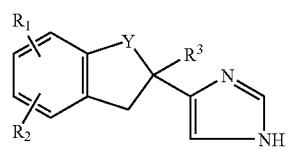

(I)

wherein Y is —$CH_2$— or —CO—, $R_1$ is H, halo or hydroxy, $R_2$ is H or halo, and $R_3$ is H or lower alkyl (e.g. $C_1$ to $C_4$ alkyl, preferably $C_1$ or $C_2$ alkyl), or a pharmaceutically acceptable salt, such as an acid addition salt, e.g. the hydrochloride, of a compound of the general formula (I), so as to promote pre-gastric absorption of the active ingredient.

The term "pre-gastric absorption" is used to refer to the absorption of the active ingredient into that part of the alimentary canal prior to the stomach and includes buccal, sublingual, oropharyngeal and oesophageal absorption.

It is envisaged that such pre-gastric absorption will occur primarily in the mucus membranes in the mouth, pharynx and oesophageal mucus membranes. It is therefore preferred that the composition of the invention should be in a form which sustains the active ingredient in contact with the buccal, sublingual, pharyngeal and/or oesophageal mucus membranes.

One example of a fast-dispersing dosage form is described in U.S. Pat. No. 4,855,326 in which a melt spinnable carrier agent, such as sugar, is combined with an active ingredient and the resulting mixture spun into a "candy-floss" preparation. The spin "candy-floss" product is then compressed into a rapidly dispersing, highly porous solid dosage form.

U.S. Pat. No. 5,120,549 discloses a fast-dispersing matrix system which is prepared by first solidifying a matrix-forming system dispersed in a first solvent and subsequently contacting the solidified matrix with a second solvent that is substantially miscible with the first solvent at a temperature lower than the solidification point of the first solvent, the matrix-forming elements and active ingredients being substantially insoluble in the second solvent, whereby the first solvent is substantially removed resulting in a fast-dispersing matrix.

U.S. Pat. No. 5,079,018 discloses a fast-dispersing dosage form which comprises a porous skeletal structure of a water soluble, hydratable gel or foam forming material that has been hydrated with water, rigidified in the hydrated state with a rigidifying agent and dehydrated with a liquid organic solvent at a temperature of about 0° C. or below to leave spaces in place of hydration liquid.

Published International Application No. WO 93/12769 (PCT/JP93/01631) describes fast-dispersing dosage forms of very low density formed by gelling, with agar, aqueous systems containing the matrix-forming elements and active ingredient, and then removing water by forced air or vacuum drying.

U.S. Pat. No. 5,298,261 discloses fast-dispersing dosage forms which comprise a partially collapsed matrix network that has been vacuum-dried above the collapse temperature of the matrix. However, the matrix is preferably at least partially dried below the equilibrium freezing point of the matrix.

Published International Application No. WO 91/04757 (PCT/US90/05206) discloses fast-dispersing dosage forms which contain an effervescent disintegration agent designed to effervesce on contact with saliva to provide rapid disintegration of the dosage form and dispersion of the active ingredient in the oral cavity.

Published International Patent Application No. WO 00/67694 discloses fast-dispersing dosage forms produced by supplying a liquid containing a biodissolvable carrier to an outlet, establishing an electric field between the outlet and a support surface to cause the liquid issuing from the outlet to form at least one fibre or fibrils of the biodissolvable carrier, which fibre or fibrils deposit(s) onto the surface to form a fibre web or mat; separating the web or mat into a plurality of individual tablets; and incorporating at least one active ingredient in and/or on the tablets. The active ingredient may be incorporated into the liquid containing the biodissolvable carrier or it may be applied (e.g. by spraying) onto the fibre or fibrils, the mat or web and/or the individual tablets.

The examples of fast-dispersing dosage forms described previously are by no means exhaustive and a substantial number of dosage forms capable of fast dispersion or disintegration will also be known to those skilled in the art of developing said dosage systems. Such systems like those described above are based on direct compression, tableting or lyophilisation techniques, and others are based on "Thin Film" or wafer technologies.

Further examples of fast dispersing or fast dissolving dosage forms based on direct compression, tableting or lyophilisation include but are not limited to Antares Pharma's Easy Tec™ tablets described in EP Patent No 0 974 365 in which an acrylic type polymer is used as a rapid tablet disintegrant, Capricorn Pharma's rapid melt molded tablets described in U.S. Pat. No. 6,375,982 which describes a novel semi-solid molded composition, CLL Pharma's FastOral® tablets described in International Patent Application WO 01/19336 which details a fast disintegrating tablet based on a loosely compressible diluting agent, Eurand's Adva Tab™ Rapidly disintegrating tablet described in EP Patent Application No 0 914 818 which details a tablet formulation based on a sugar alcohol or saccaride of average particle size of not more than 30 µm and a disintegrant, KV Pharmaceutical Company's Oraquick™ fast dissolving delivery system described in U.S. Pat. No. 6,284,270 which details a rapidly disintegrating tablet for use without water and Sato Pharmaceutical's SATAB technology described in U.S. Pat. No. 6,316,026 which details a formulation and a process capable of yielding tablets with rapid disintegration in the mouth.

Yet further examples of fast dispersing or dissolving drug delivery systems are based on 'Thin Film' technology. These include but are not limited to Kosmos Pharma's FDTAB™ films described in International Patent Application WO 03/030881 which describes an ingestible water soluble delivery system in the form of a film composition comprising a glucan and a water soluble polymer, Lavipharm Laboratories Quick-Dis™ drug delivery system described in U.S. Pat. No. 6,552,024 which details a mucosal surface coating film dosage unit containing a water soluble hydrocolloid, an effective dose of active ingredient and a mucosal adhesion enhancer and LTS Lohmann's Buccal wafers described in U.S. Pat. No. 5,948,430 which describes a water soluble film comprising water soluble polymers for oral administration with instant wettability The term "fast-dispersing dosage form" therefore encompasses all the types of dosage forms described in the preceding paragraphs. However, it is particularly preferred that the fast-dispersing dosage form is of the type described in U.K. Pat. No. 1,548,022, that is, a solid, fast-dispersing network of the active ingredient and a water-soluble or water-dispersible carrier which is inert towards the active ingredient, the network having been obtained by subliming solvent from a composition in the solid state, that composition comprising the active ingredient and a solution of the carrier in a solvent.

It is preferred that the composition of the invention disintegrates within 10 seconds, particularly less than 8 seconds, of being placed in the oral cavity.

In the case of the preferred type of fast-dispersing dosage form described above, the composition will preferably contain, in addition to the active ingredient, matrix forming agents and secondary components. Matrix forming agents suitable for use in the present invention include materials derived from animal or vegetable proteins, such as the gelatins, dextrins and soy, wheat and psyllium seed proteins; gums such as acacia, guar, agar, and xanthan; polysaccharides; alginates; carboxymethylcelluloses; carrageenans; dextrans; pectins; synthetic polymers such as polyvinylpyrrolidone; and polypeptide/protein or polysaccharide complexes such as gelatin-acacia complexes. The use of gelatin, particularly fish gelatin, is preferred.

Other matrix forming agents suitable for use in the present invention include sugars such as mannitol, dextrose, lactose, galactose and trehalose; cyclic sugars such as cyclodextrin (including derivatives thereof, such as hydroxy propyl-β-cyclodextrin); inorganic salts such as sodium phosphate, sodium chloride and aluminium silicates; and amino acids having from 2 to 12 carbon atoms such as L-glycine, L-alanine, L-aspartic acid, L-glutamic acid, L-hydroxyproline, L-isoleucine, L-leucine and L-phenylalanine. The use of glycine particularly in combination with mannitol is preferred.

One or more matrix forming agents may be incorporated into the solution or suspension prior to solidification. The matrix forming agent may be present in addition to a surfactant or to the exclusion of a surfactant. In addition to forming the matrix, the matrix forming agent may aid in maintaining the dispersion of the active ingredient within the solution or suspension. This is especially helpful in the case of active agents that are not sufficiently soluble in water and must, therefore, be suspended rather than dissolved.

Secondary components such as preservatives, antioxidants, surfactants, viscosity enhancers, colouring agents, flavouring agents, sweeteners or taste-masking agents may also be incorporated into the composition. Suitable colouring agents include red, black and yellow iron oxides and FD & C dyes such as FD & C blue No. 2 and FD & C red No. 40 available from Ellis & Everard. Suitable flavouring agents include mint, raspberry, liquorice, orange, lemon, grapefruit, caramel, vanilla, cherry and grape flavours and combinations of these. Suitable sweeteners include aspartame, acesulfame K and thaumatin. Suitable taste-masking agents include sodium bicarbonate, ion-exchange resins, cyclodextrin inclusion compounds, adsorbates or microencapsulated actives.

It is preferred not to include a pH modifier such as sodium hydroxide because this can cause unwanted precipitation and aggregation of the active ingredient during preparation of the solid dosage form. The acid addition salt, particularly the hydrochloride salt, of the compound of the formula (I) is preferred for incorporation into the solid dosage form.

In the general formula (I) above:
$R_1$ is preferably halo, more preferably fluoro, and most preferably 5-fluoro;
$R_2$ is preferably H;
$R_3$ is preferably ethyl;
Y is preferably —$CH_2$—.

The invention will now be described, in further detail, in the following Examples.

Liquid formulations having the compositions illustrated in Table 1 below (all amounts in % w/w) were made up by adding the fish gelatin slowly to the purified water and allowing sufficient time to dissolve whilst maintaining stirring throughout the process up to and including the dosing stage to be described hereinafter. Upon complete dissolution of the fish gelatin, the mannitol was added and allowed to dissolve. Following this, the glycine was added (where applicable) and allowed to dissolve. The mint flavour and sweetener were then added. Once these had been fully dispersed, the active ingredient, fipamezole, being one of the examples for the compounds of the present invention, was added to produce the final solution.

TABLE 1

Formulations

| Ingredient | Example No. | | | | | | |
|---|---|---|---|---|---|---|---|
| | 1 | 2 | 3 | 4 | 5 | 6 | 7 |
| fipamezole[1] | 4.00 | 4.00 | 4.00 | 4.00 | 4.00 | 4.00 | 5.00 |
| Fish Gelatin[2] (3101) | 5.25 | 5.00 | 5.25 | 5.00 | 5.25 | 6.30 | 6.30 |
| Mannitol EP/USP | 4.00 | 3.75 | 4.00 | 3.75 | 4.00 | 4.8 | 4.80 |
| Glycine EP/USP | 2.00 | 2.00 | 2.00 | — | 2.00 | 2.50 | 1.00 |
| Mint (powdered) | — | 0.20 | 0.25 | 0.20 | — | 0.75 | 0.75 |
| Mint (liquid) | 0.50 | — | — | — | 0.50 | — | — |
| Acesulfame K | 0.50 | 0.25 | 0.25 | 0.25 | — | — | — |
| Aspartame | — | — | — | — | 0.50 | 0.75 | 0.75 |
| Purified Water EP/USP | $Q_s$ 100 | $Q_s$ 100 | $Q_s$ 100 | $Q_s$ 100 | $Q_s$ 100 | $Q_s$ 100 | $Q_s$ 100 |

[1] 4-(2-ethyl-5-fluoro-indan-2-yl)-1H-imidazole, hydrochloride salt.
[2] Supplied by Croda Colloids Ltd (non-hydrolysed, spray dried fish gelatin)
$Q_s$ = sufficient to give.

The above-prepared solutions were dosed into pre-formed multilayer blister packs of the required dose size (variously 20 mg and 40 mg, or 10 mg and 30 mg in the case of formulation Examples 6 & 7. 80 mg dosage forms were also prepared using the described composition (data not shown). Once dosed, the filled blister packs were passed through a liquid nitrogen freeze tunnel to ensure a frozen product. The frozen products were immediately placed in temporary storage at −25° C. (±5° C.) prior to freeze drying. The dosed solutions were subsequently freeze dried using a temperature of +20° C. and a chamber pressure of 0.5 mbar. After freeze-drying, a paper-foil composite lidding material was used to seal the final dried product in the blister packs.

Comparing Example 4 with the remaining Examples, notably Example 2, it was noted that the presence of glycine had a beneficial effect on the appearance and structured properties of the solid fast-dispersing dosage forms. Examples 1, 3, 5, 6 and 7 had increased levels of the main structural excipients (gelatin and mannitol) and exhibited a marginal improvement over Examples 2 and 4 which left a thin layer of residue when the dosage forms were removed from their pockets in the blister pack.

Disintegration tests indicated that the fast-dispersing tablets had a disintegration time in the oral cavity of less than 2 to 3 seconds and the packaged tablets were suitably stable after four weeks storage.

Pharmacokinetic Studies
1. Comparison of Buccal vs Oral Administration in Humans Improved absorption by the pre-gastric route was demonstrated by comparison between oral administration of fipamezole as a solution and administration as a buccal spray.

Protocol A (Comparative Example)

Fipamezole was administered orally in solution in increasing doses (0.5, 1, 3, 9, 18, 30 and 60 mg) to healthy volunteers (Caucasian males, 18-35 years old, 60-90 kg body weight). Blood samples were taken at intervals for pharmacokinetic evaluation up to 24 hours after each dose. Concentrations of fipamezole in plasma were measured with HPLC-MS/MS. Safety and tolerability were evaluated by standard safety laboratory determinations, ECG recordings, blood pressure and heart rate measurements and by adverse event questioning.

The pharmacokinetics were evaluated using the Topfit 2.0 pharmacokinetic program. $C_{max}$ and $t_{max}$ were read from the concentration vs. time curves and the apparent elimination phase half lives from the semi-logarithmic terminal part of the curve. AUC values were calculated both for infinity and up to the last measurable data point. The study had a parallel-group double-blind placebo-controlled design.

Fipamezole was found to be safe and well tolerated. The pharmacokinetic data is shown in Table 2 below, from which it can be seen that the peak plasma concentrations of fipamezole achieved were small (about 2 ng/ml) even after the highest 60 mg oral dose. The level of absorption is not dose-proportional, suggesting that bioavailability of non-metabolised fipamezole by the oral route is unsatisfactory.

TABLE 2

Pharmacokinetics of fipamezole administered orally as a solution

| Dose (mg) | $C_{max}$ (ng/ml) | $t_{max}$ (hr) | $t_{1/2}$ (hr) | $AUC_t$ (ng-hr/ml) |
|---|---|---|---|---|
| 0.5 | 0.05 | 0.88 | — | — |
| 1 | 0.08 | 0.83 | — | 0.1 |
| 3 | 0.23 | 0.67 | — | 0.3 |
| 9 | 1.09 | 0.67 | 2.2 | 4.2 |
| 18 | 1.31 | 0.83 | 2.4 | 6.0 |
| 30 | 1.59 | 1.25 | 3.1 | 6.8 |
| 60 | 1.97 | 1.06 | 1.8 | 8.2 |

Protocol B (Buccal Spray)

The protocol used was substantially as for protocol A, except administration was by buccal spray (0.75, 1.5, 3, 7.5, 15, 30, 60 and 90 mg single doses).

All doses were found to be well tolerated with no other adverse effects than buccal erythema and whitening, which were frequently seen after administration. The pharmacokinetic data are shown in Table 3.

TABLE 3

Pharmacokinetics of fipamezole administered as a buccal spray

| Dose (mg) | $C_{max}$ (ng/ml) | $t_{max}$ (hr) | $t_{1/2}$ (hr) | $AUC_t$ (ng-hr/ml) |
|---|---|---|---|---|
| 0.75 | 1.53 | 0.72 | 1.47 | 4.60 |
| 1.5 | 3.13 | 0.72 | 1.65 | 9.99 |
| 3 | 4.76 | 0.78 | 1.60 | 15.4 |
| 7.5 | 13.00 | 0.72 | 1.78 | 40.8 |
| 15 | 25.93 | 0.72 | 1.97 | 84.1 |
| 30 | 49.23 | 0.72 | 2.12 | 157 |
| 60 | 92.93 | 0.46 | 3.00 | 231 |
| 90 | 172.0 | 0.53 | 3.16 | 467 |

As can be seen fipamezole was rapidly absorbed in a dose-dependent manner from the buccal mucosa into systemic circulation. The apparent elimination phase half life ranged from about 1.2 to 3.5 hours, with the longer times corresponding to the larger doses. There was a linear correlation between the fipamezole dose and $C_{max}$ and $AUC_{0-inf}$ values.

2. Pharmacokinetics of Fast Dispersing Dosage Form in Dogs

In this study fipamezole was administered orally as a fast dispersing tablet (formulation as for Example 3 above) (20 mg/kg) via the buccal cavity to pure bred beagle dogs (1 male and 1 female). Throughout the study (8 days, and 4 days pre-study) the subjects were monitored for viability, changes in behaviour, reaction to treatment and ill-health. In addition, body weight and food consumption were recorded. Blood was collected at 10, 20, 30 and 45 minutes and 1, 1.25, 1.5, 2, 2.5, 3, 4 and 8 hours after administration for plasma level analysis (LC/MS/MS method).

No adverse clinical signs were observed in the female (the male showed elevated pulse rate). There was no adverse effect on body weight, although food consumption on the day of administration was low, probably due to the frequent collection of blood.

Referring to the drawing, which is a graph plotting plasma concentration against time, it can be seen that fipamezole was rapidly absorbed, with peak plasma concentration being reached within 10 minutes.

3. Comparison Between Buccal Spray and Fast Dissolving Tablet

The buccal spray and fast dissolving dosage form were directly compared by administration of a single 30 mg dose of fipamezole to two sets of human subjects. In contrast to the finding described above for Buccal Spray, buccal erythema and whitening was not observed with the fast dissolving dosage forms which therefore offer advantages in terms of patient compliance. The results are shown in Table 4. As can be seen from Table 4, the mean maximum plasma concentration ($C_{max}$) for the fast dissolving tablet was lower, but the standard deviation (SD) and coefficient of variance (CV %) were also lower. This effect was confirmed in a subsequent trial (12 subjects) in which the $C_{max}$ SDs were 26.2 and 13.5 for buccal spray and fast dissolving dosage form respectively. The lower SD and CV % suggest that it may be easier to control the targeted $C_{max}$ if administration is by the fast dissolving tablet which therefore offers advantages in terms of patient safety.

TABLE 4

$C_{max}$ Following Single Dose Administration of 30 mg of fipamezole

| Buccal Spray | | Fast dissolving tablet | |
|---|---|---|---|
| Subject | $C_{max}$ (ng/ml) | Subject | $C_{max}$ (ng/ml) |
| 1 | 110.68 | 1 | 40.77 |
| 2 | 32.28 | 2 | 30.74 |
| 3 | 31.14 | 3 | 12.45 |
| 4 | 38.04 | 4 | 27.42 |
| 5 | 50.72 | 5 | 34.05 |
| 6 | 44.93 | 6 | 26.67 |
| 7 | 50.13 | 7 | 37.12 |
| N | 7 | N | 7 |
| Mean | 51.13 | Mean | 29.89 |
| SD | 27.42 | SD | 9.21 |
| CV % | 53.6% | CV % | 30.8% |

The invention claimed is:

1. A fast-dispersing, solid dosage form comprising:
a substituted imidazole derivative of general formula (I)

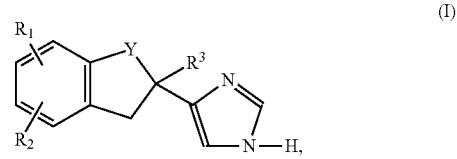

or a pharmaceutically acceptable salt of a compound of the general formula (I) as an active ingredient, and
    one or more matrix forming agents comprising one or more of gelatin and a sugar,
    wherein Y is —CH$_2$— or —CO—, R$_1$ is halo or hydroxy, R$_2$ is H or halo, and R$_3$ is H or lower alkyl,
    wherein the fast-dispersing, solid dosage form is formulated to promote pre-gastric absorption of the active ingredient and to disintegrate within 10 seconds of being placed in the oral cavity, and
    wherein the fast-dispersing, solid dosage form is a freeze-dried solid dosage form.

2. The fast-dispersing, solid dosage form as claimed in claim 1, which comprises a network of the active ingredient and a water-soluble or water-dispersible carrier which is inert towards the active ingredient, the network having been obtained by subliming solvent from a composition in the solid state, said composition comprising the active ingredient and a solution of the carrier in a solvent.

3. The fast-dispersing, solid dosage form as claimed in claim 1, wherein the matrix forming agents comprise gelatin and at least one sugar.

4. The fast-dispersing, solid dosage form as claimed in claim 3, wherein the gelatin is fish gelatin.

5. The fast-dispersing, solid dosage form as claimed in claim 3, wherein the sugar is mannitol.

6. The fast-dispersing, solid dosage form as claimed in claim 3, wherein the matrix forming agent(s) includes an amino acid.

7. The fast-dispersing, solid dosage form as claimed in claim 1, wherein the matrix forming agent(s) includes an amino acid.

8. The fast-dispersing, solid dosage form as claimed in claim 7, wherein the amino acid is glycine.

9. The fast-dispersing, solid dosage form as claimed in claim 1, wherein Y is —CH$_2$—.

10. The fast-dispersing, solid dosage form as claimed in claim 1, wherein $R_1$ is halo or hydroxy.

11. The fast-dispersing, solid dosage form as claimed in claim 1, wherein $R_1$ is halo.

12. The fast-dispersing, solid dosage form as claimed in claim 1, wherein $R_1$ is 5-halo.

13. The fast-dispersing, solid dosage form as claimed in claim 1, wherein $R_1$ is fluoro.

14. The fast-dispersing, solid dosage form as claimed in claim 1, wherein $R_2$ is hydrogen.

15. The fast-dispersing, solid dosage form as claimed in claim 1, wherein $R_3$ is ethyl.

* * * * *